United States Patent [19]

Glover et al.

[11] Patent Number: 4,994,743
[45] Date of Patent: Feb. 19, 1991

[54] METHOD FOR MONITORING RESPIRATION WITH ACQUIRED NMR DATA

[75] Inventors: Gary H. Glover, Delafield; Stephen W. Flax, Wauwatosa, both of Wis.; Ann Shimakawa, San Francisco, Calif.

[73] Assignee: General Electric Company, Milwaukee, Wis.

[21] Appl. No.: 427,401

[22] Filed: Oct. 27, 1989

[51] Int. Cl.$^5$ .......................................... G01R 33/20
[52] U.S. Cl. .................................... 324/309; 324/306
[58] Field of Search ............... 324/300, 307, 306, 309, 324/310, 311, 312, 313, 314, 318, 322; 128/653 A, 653 AF

[56] References Cited

U.S. PATENT DOCUMENTS

| Re. 32,701 | 6/1988 | Moran | 324/309 |
| 4,564,017 | 1/1986 | Glover | 128/653 |
| 4,567,893 | 2/1986 | Charles et al. | 128/653 |
| 4,710,717 | 12/1987 | Pelc et al. | 324/309 |
| 4,724,386 | 2/1988 | Haacke et al. | 324/309 |
| 4,761,613 | 8/1988 | Hinks | 324/309 |
| 4,857,846 | 8/1989 | Carlson | 324/309 |
| 4,937,526 | 6/1990 | Ehman | 324/309 |

Primary Examiner—Michael J. Tokar
Attorney, Agent, or Firm—Quarles & Brady

[57] ABSTRACT

NMR data indicative of the motion of the anterior abdominal wall of a subject is acquired just prior to each image data pulse sequence in an NMR scan. The acquired motion NMR data is processed on-line to produce a signal indicative of the displacement of the abdominal wall from a reference position. The displacement values may be employed to produce a signal indicative of a respiration phase that can be used in connection with motion artifact reduction techniques.

6 Claims, 5 Drawing Sheets

METHOD FOR MONITORING RESPIRATION WITH ACQUIRED NMR DATA

BACKGROUND OF THE INVENTION

This invention relates to nuclear magnetic resonance imaging methods. More specifically, this invention relates to a method for controlling image artifacts caused by substantially periodic NMR signal variations due, for example, to subject motion in the course of an NMR scan.

NMR has been developed to obtain images of anatomical features of human patients. Such images depict nuclear spin distribution (typically, protons associated with water and tissue), spin-lattice relaxation time $T_1$, and/or spin-spin relaxation time $T_2$ and are of medical diagnostic value. NMR data for constructing images can be collected using one of many available techniques, such as multiple angle projection reconstruction and Fourier transform (FT). Typically, such techniques comprise a pulse sequence made up of a plurality of sequentially implemented views. Each view may include one or more NMR experiments, each of which comprises at least an RF excitation pulse and a magnetic field gradient pulse to encode spatial information into the resulting NMR signal. As is well-known, the NMR signal may be a free induction decay (FID) or, preferably, a spin-echo signal.

The preferred embodiments of the invention will be described in detail with reference to a variant of the well known FT technique, which is frequently referred to as "spin-warp". It will be recognized, however, that the method of the invention is not limited to FT imaging methods, but may be advantageously practiced in conjunction with other techniques, such as multiple angle projection reconstruction disclosed in U.S. Pat. No. 4,471,306, and another variant of the FT technique disclosed in U.S. Pat. No. 4,070,611. The spin-warp technique is discussed in an article entitled "Spin Warp NMR Imaging and Applications to Human Whole Body Imaging" by W. A. Edelstein et al., *Physics in Medicine and Biology*, Vol 25, pp. 751–756 (1980).

Briefly, the spin-warp technique employs a variable amplitude phase encoding magnetic field gradient pulse prior to the acquisition of NMR spin-echo signals to phase encode spatial information in the direction of this gradient. In a two-dimensional implementation (2DFT), for example, spatial information is encoded in one direction by applying a phase-encoding gradient ($G_y$) along that direction, and then observing a spin-echo signal in the presence of a magnetic field gradient ($G_x$) in a direction orthogonal to the phase-encoding direction. The gradient present during the spin-echo encodes spatial information in the orthogonal direction. In a typical 2DFT pulse sequence, the magnitude of the phase-encoding gradient pulse $G_y$ is incremented ($\Delta G_y$) monotonically in the sequence of views that are acquired to produce a set of NMR data from which an entire image can be reconstructed.

Object displacement during the acquisition of NMR image data produces both blurring and "ghosts" in the phase-encoded direction. Discrete ghosts are particularly apparent when the motion is periodic, or nearly so, while smearing occurs when the motion is aperiodic. For most physiological motion, including cardiac and respiratory motion, each view of the NMR signal is acquired in a period short enough that the object may be considered stationary during the acquisition window. Blurring and ghosts are, therefore, due primarily to the inconsistent appearance of the object from view to view, and in particular, due to changes in the amplitude and/or phase of the NMR signal due to the motion.

Both blurring and ghosts can be reduced if the data acquisition is synchronized with the functional cycle of the object. This method is known as gated NMR scanning, and its objective is to acquire NMR data at the same point during successive functional cycles so that the object "looks" the same in each view. The drawback of gating is that NMR data may be acquired only during a small fraction of the object's functional cycle, and even when the shortest acceptable pulse sequence is employed, the gating technique can significantly lengthen the data acquisition time.

One proposed method for eliminating ghost artifacts is disclosed in U.S. Pat. No. 4,567,893, issued on Feb. 4, 1986, and which is assigned to the same assignee as the present invention. In this prior patent, it is recognized that with the periodic motion the distance in the image between the ghosts and the object being imaged is maximized when the NMR pulse sequence repetition time is an odd multiple of one-fourth of the duration of the periodic signal variation (if two phase-alternated RF excitation pulses per view are used, as disclosed and claimed in commonly assigned U.S. Pat. No. 4,443,760, issued Apr. 17, 1984). It is recognized that this ratio can be used to alleviate ghosts due to respiratory motion. While this method, indeed, improves image quality, it does impose a constraint on the NMR pulse sequence repetition time and it often results in a longer total scan time. It also assumes that the motion is periodic. Its effectiveness is diminished when the subject's breathing is irregular because the ghosts are blurred and can overlap the image region of interest.

Another method for reducing the undesirable effects due to periodic signal variations is disclosed in U.S. Pat. No. 4,706,026 issued on Nov. 10, 1987 and entitled "A Method For Reducing Image Artifacts Due To Periodic Variations In NMR Imaging." In one embodiment of this method, an assumption is made about the signal variation period (e.g. due, for example, to patient respiration) and the view order is altered from the usual monotonically increasing phase-encoding gradient to a preselected order. This involves establishing the order in which either the gradient parameters, i.e. the amplitude of the phase-encoding gradient pulses (in the spin-warp method) or the direction of the read-out gradient pulses (in the multiple angle projection reconstruction method) are implemented. For a given signal variation period, a view order is chosen so as to make the NMR signal variation as a function of the phase-encoding amplitude (or gradient direction) be at a desired frequency. In one embodiment, the view order is selected such that the motion variation period appears to be equal to the total NMR scan time (low frequency) so that the ghost artifacts are brought as close to the object being imaged as possible. In another embodiment (high frequency), the view order is chosen to make the variation period appear to be as short as possible so as to push the ghost artifacts as far from the object as possible.

This prior method is effective in reducing artifacts, and is in some respects ideal if the variation is rather regular and at a known frequency. On the other hand, the method is not very robust if the assumption made about the motion temporal period does not hold (e.g., because the patient's breathing pattern changes or is irregular). If this occurs, the method loses some of its effectiveness because the focusing of the ghosts, either as close to the object or as far from the object as possible, becomes blurred. A solution to this problem is disclosed in U.S. Pat. No. 4,663,591 which issued on May 5, 1987 and is entitled "A Method For Reducing Image Artifacts Due To Periodic Signal Variations in NMR Imaging." In this method, the non-monotonic view order is determined as the scan is executed and is responsive to changes in the period so as to produce a desired relationship (low frequency or high frequency) between the signal variations and the gradient parameter. The effectiveness of this method, of course, depends upon the accuracy of the means used to sense the patient motion, and particularly, any amplitude variations in the periodicity of that motion.

One common means used to monitor respiratory motion of a patient undergoing an NMR scan is comprised of a pneumatic bellows with a pressure sensor which is attached around the patient's chest. As the patient breaths, the anterior chest and stomach wall expand and contract and the resulting pressure change in the bellows causes the electrical signal from the pressure transducer to vary in magnitude as a function of respiratory phase. Not only is the pneumatic bellows a complicated electromechanical device which requires continuous maintenance, but it also has been discovered that the signals produced by such monitors do not always accurately indicate the respiratory movement which causes motion artifacts in NMR images.

An alternative approach to respiration monitoring is to employ NMR signals obtained during the scan to produce a signal which indicates the respiratory rate as described in U.S. Pat. No. 4,564,017. While this method provides an "on-line" measure of respiration rate by measuring the changes in magnitude of the NMR echo signal, it does not provide accurate on-line data which indicates the phase of the respiratory cycle.

SUMMARY OF THE INVENTION

The present invention relates to an improved method and system for obtaining respiratory phase information during an NMR scan for use in motion artifact suppression techniques. More specifically, the invention includes means for producing motion NMR signals during the NMR scan, means for processing the motion NMR signals to produce a data set which indicates the position of features in the subject being scanned, means for locating the position of a specific feature in said data set, and means for producing a respiratory signal by correlating the current position of the specific feature with a reference position for that feature.

A general object of the invention is to provide a more accurate indication of the movement of anatomical structures during an NMR scan. The motion detection NMR data set is acquired during the same scan used to acquire the image NMR data set and it is acquired with the very same apparatus. By using the very same NMR system to monitor respiratory motion, the effects of the motion on the NMR signals used to reconstruct an image can be more accurately measured. When used with any of a number of motion artifact suppression methods, the improved respiratory phase signal results in the reconstruction of an image which is better than that which is reconstructed using the phase information from a conventional respiration monitor.

Another object of the invention is to eliminate the need for electromechanical apparatus which must be strapped to the patient. The present invention does not require any apparatus other than that which is required to acquire the NMR data for the image. The NMR pulse sequence is altered to include acquisition of the motion detection NMR data set, but this requires no additional apparatus. The only impact on the patient is a slight increase in the time necessary to conduct the entire scan.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
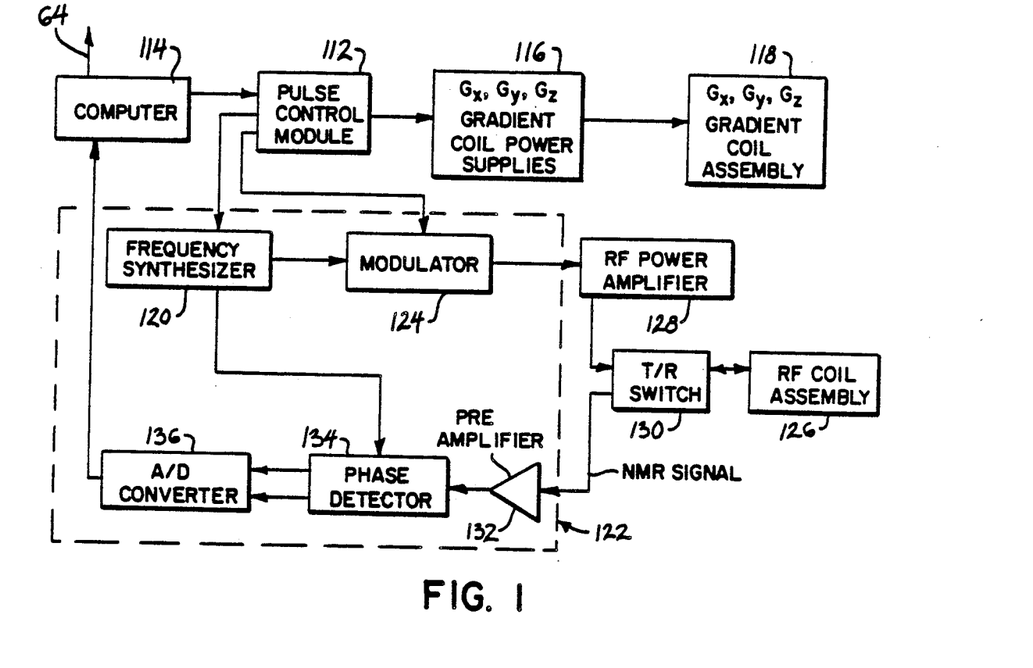
FIG. 1 is an electrical block diagram of an NMR system which employs the present invention.

FIG. 1 is a simplified block diagram of an NMR imaging system which employs the preferred embodiment of the invention. The system includes a pulse control module 112 which provides properly timed pulse waveform signals, under the control of a host computer 114, to magnetic field gradient power supplies collectively designated at 116. These power supplies 116 energize gradient coils which form part of a gradient coil assembly generally indicated by block 118. The assembly contains coils which produce the $G_x$, $G_y$ and $G_z$ magnetic field gradients directed in the x, y, and z directions, respectively, of the Cartesian coordinate system. The use of the $G_x$, $G_y$ and $G_z$ gradients in NMR imaging applications will be described hereinafter with reference to FIG. 2.

Continuing with reference to FIG. 1, the pulse control module 112 provides activating pulses to an RF synthesizer 120 which is part of an RF transceiver, portions of which are enclosed by dash-line block 122. The pulse control module 112 also supplies signals to a modulator 124 which modulates the output of the RF frequency synthesizer 120. The modulated RF signals are applied to an RF coil assembly 126 through an RF power amplifier 128 and a transmit/receive switch 130.

The RF signals are used to excite nuclear spins in a sample object (not shown) which is to be imaged.

Figure 2:
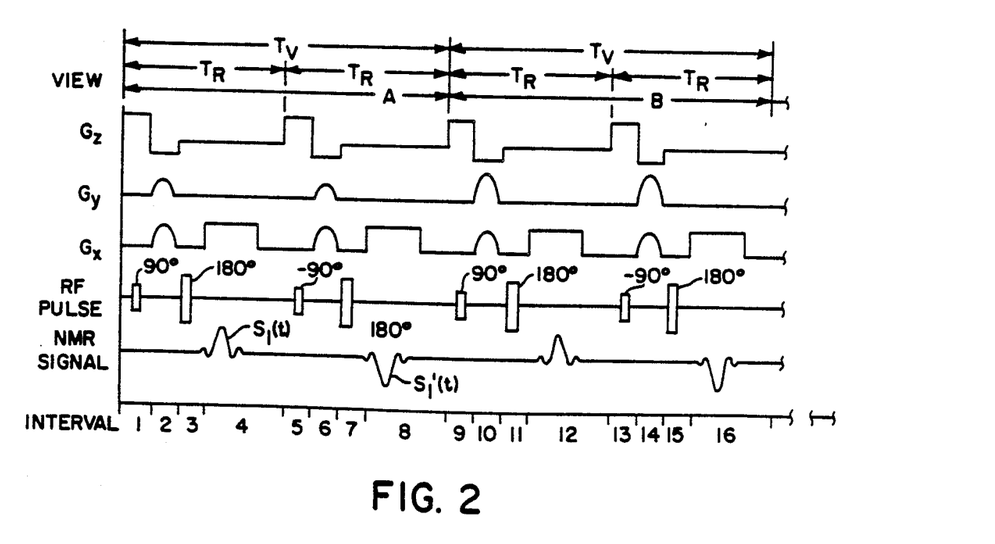
FIG. 2 is an exemplary imaging pulse sequence which is executed by the system of FIG. 1.

Reference is made to FIG. 2 which depicts two views of a conventional imaging pulse sequence of the type known as two-dimensional Fourier transforms (2DFT), and which is also referred to as two-dimensional "spin-warp". This pulse sequence is useful in obtaining, in a well known manner, imaging NMR data to reconstruct images of an object being investigated. The two views are indicated at "A" and "B" and they are identical with the exception of the phase-encoding gradient field $G_y$. Each view is a pulse sequence which utilizes phase-alternated RF excitation pulses which, as disclosed and claimed in the above-identified U.S. Pat. No. 4,443,760, produce phase-alternated NMR signals $S_1(t)$ and $S_1'(t)$ to cancel certain baseline errors in the NMR system.

Referring now to View A in FIG. 2, there is shown in interval 1 (indicated along the horizontal axis) a selective 90° RF excitation pulse applied in the presence of a positive $G_z$ magnetic field gradient pulse. Pulse control module 112 (FIG. 1) provides the needed control signals to the frequency synthesizer 120 and modulator 124 so that the resulting excitation pulse is of the correct phase and frequency to excite nuclear spins only in a predetermined region of the object being imaged. Typically, the excitation pulse can be amplitude modulated by a (sin x)/x function. The frequency of the synthesizer 120 is dependent on the strength of the applied polarizing magnetic field and the particular NMR species being imaged in accordance with the well known Larmor equation. The pulse control module 112 also applies activating signals to the gradient power supplies 116 to generate, in this case, the $G_z$ gradient pulse.

Continuing with reference to FIG. 2, $G_x$, $G_y$ and $G_z$ gradient pulses are applied simultaneously in interval 2. The $G_z$ gradient in interval 2 is a rephasing pulse typically selected such that the time integral of the gradient waveform over interval 2 is approximately equal to $-\frac{1}{2}$ of the time integral of the $G_z$ gradient waveform over interval 1. The function of the negative $G_z$ pulse is to rephase the nuclear spins excited in interval 1. The $G_y$ gradient pulse is a phase-encoding pulse selected to have a different amplitude in each of Views A, B, ..., etc., to encode spatial information in the direction of the gradient. The number of different $G_y$ gradient amplitudes is typically selected to equal at least the number of pixel resolution elements the reconstructed image will have in the phase-encoding (Y) direction. Typically, 128, 256, or 512 different gradient amplitudes $G_y$ are selected and in the typical NMR system, the $G_y$ values are incremented a fixed amount from one view to the next until the NMR scan is complete.

The $G_x$ gradient pulse in interval 2 is a dephasing pulse needed to dephase the excited nuclear spins by a predetermined amount to delay the time of occurrence of a spin-echo signal $S_1(t)$ in interval 4. The spin-echo signal is produced typically by the application of a 180° RF pulse in interval 3. As is known, the 180° RF pulse is a pulse which reverses the direction of spin dephasing so as to produce the spin-echo signal. The spin-echo signal is sampled in interval 4 in the presence of a gradient pulse $G_x$ to encode spatial information in the direction (X) of this gradient.

As indicated above, baseline error components are eliminated by using an additional NMR measurement in each view. This second measurement is substantially identical to the first with the exception that the RF excitation pulse in interval 5 of View A is selected to be 180° out of phase (as suggested by the minus sign) relative to the excitation pulse in interval 1 of View A. As a result, the spin-echo signal $S_1'(t)$ in interval 8 is 180° out of phase with the spin-echo signal $S_1(t)$ in interval 4. If the signal $S_1'(t)$ is subtracted from $S_1(t)$, only those components of the signals with reversed sign in the signal $S_1'(t)$ are retained. The baseline error components thus cancel.

The process described above with reference to View A is repeated for View B and so on for all amplitudes of the phase-encoding $G_y$ gradient. The NMR image data which is collected during this scan is stored in the host computer 114 where it is processed to produce image data suitable for controlling a CRT display.

As the above described conventional NMR scan is performed, NMR data is acquired from all physical locations within the plane, or slice, of the object being imaged. If an accurate image is to be reconstructed, then both the object and the measurement conditions must be stable, or fixed, during the time needed to complete the entire NMR scan. The present invention deals with the very practical situations in which this is not the case, but instead, the measurement conditions change in some cyclic, or nearly cyclic, manner.

One such situation occurs when an image is to be produced through the abdomen of a human subject. In this case, much of the material being imaged is in motion due to the subject's breathing, and the time needed to acquire the NMR data for an entire image will often transcend many respiration cycles. If NMR data is acquired continuously throughout the respiration cycles, the subject will be disposed differently from view to view and the reconstructed image will contain many motion artifacts.

The present invention is an improvement to an NMR system which enables it to acquire NMR data that indicates the motion of the subject due to respiration and which processes that motion NMR data to produce a respiration monitor signal. As indicated above, the respiration monitor signal may be used in any of a number of known motion artifacts suppression techniques.

Figure 3:
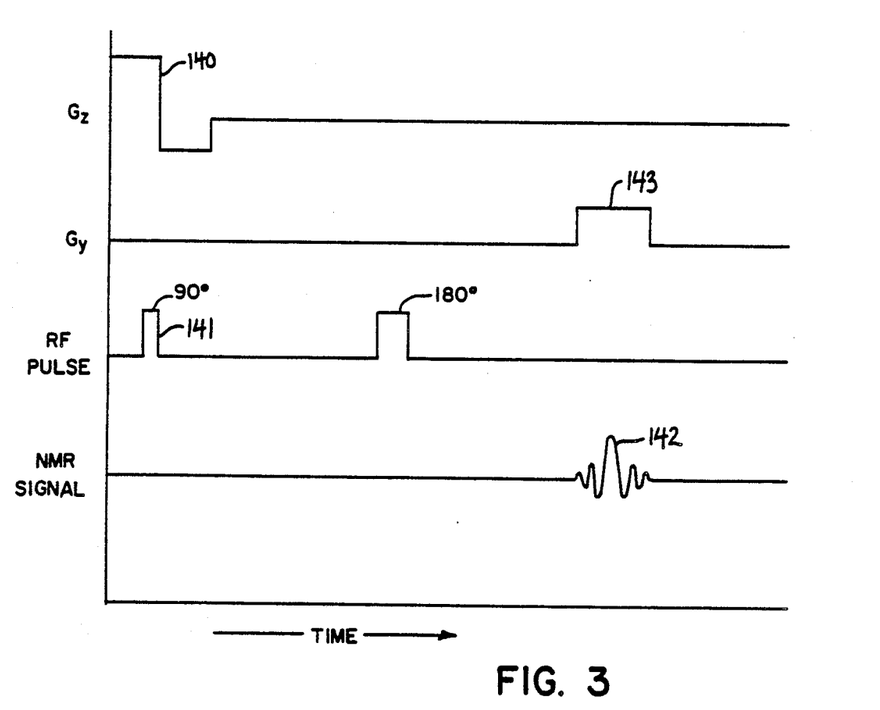
FIG. 3 is a preferred embodiment of the motion pulse sequence of the present invention which is interleaved with the imaging pulse sequence of FIG. 2.
Figure 4:
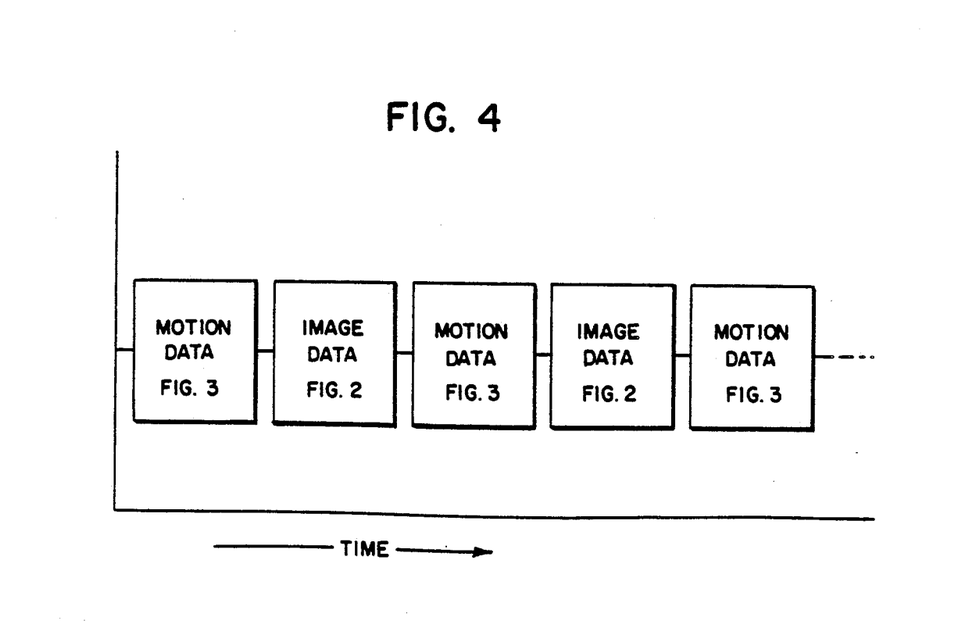
FIG. 4 is a diagram which illustrates how the motion pulse sequences interleave with the image pulse sequences.

To acquire NMR motion information during the scan, a separate pulse sequence is interleaved between each view of the image data pulse sequence of FIG. 2. This motion NMR pulse sequence is illustrated in FIG. 3 and it is executed just prior to each view of the image data pulse sequence as illustrated in FIG. 4. Referring particularly to FIG. 3, the motion NMR pulse sequence differs in a number of ways from the image data pulse sequence. For example, while a slice select gradient pulse 140 is employed during the application of an RF excitation pulse 141 to excite spins in a slice, no phase encoding gradient pulse is applied. Instead, the NMR signal 142 is acquired during a read out gradient pulse 143, which in the preferred embodiment is produced along the Y axis by the gradient field $G_y$. No X axis gradient field $G_x$ is applied so that the resulting NMR signal has no position information along the X axis. In the preferred embodiment of the invention, the R.F. excitation pulse 141 imparts a 90° flip angle to the spins and the slice select gradient pulse 40 selects the same slice as that from which image data is being acquired.

Figure 6:
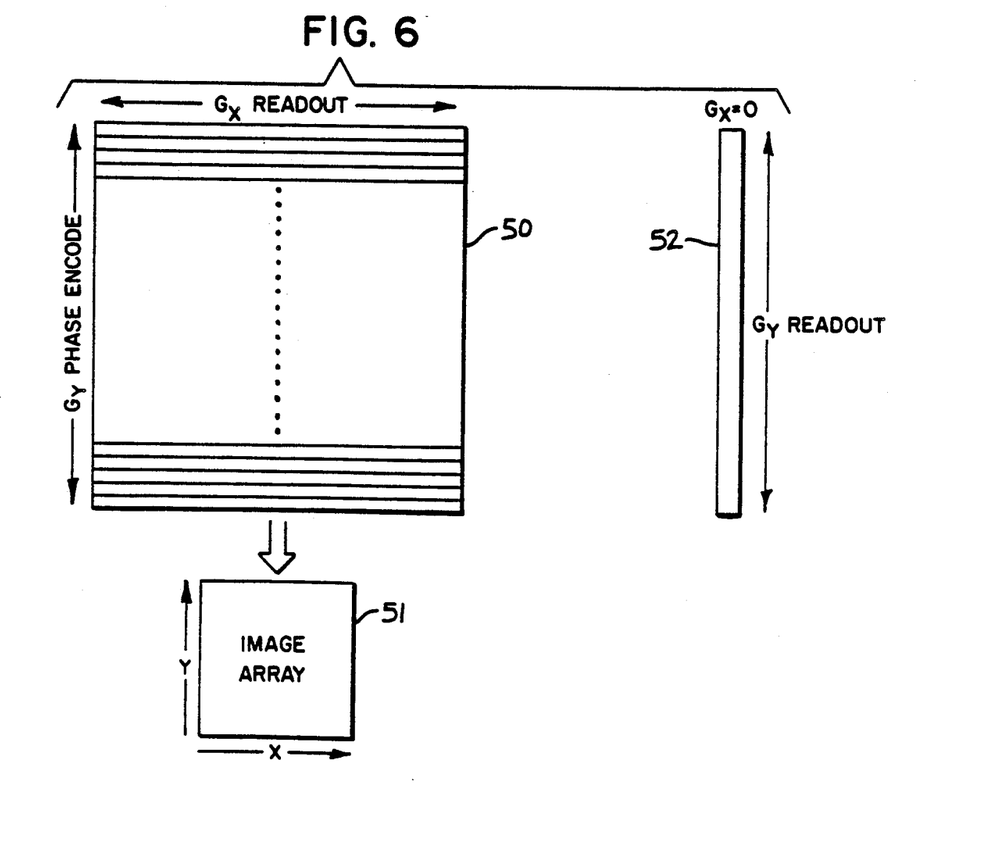
FIG. 6 is a pictorial representation of data structures produced during the data acquisition and processing steps.

The data which are acquired during the scan is illustrated in FIG. 6. The image data which is acquired is stored in a two-dimensional array 50 that has a size which is determined by the chosen resolution of the image to be produced (i.e. 128 by 128; 256 by 256 or 512 by 512 pixels). It will be understood by those skilled in the art that actually two such arrays are acquired, one containing the inphase acquired data (I), and the other containing the quadrature data (Q). Each row of data in the array 50 represents the digitized data acquired during one view, and each row is acquired with a different value of phase encoding magnetic field gradient $G_y$. When data have been acquired for each value of phase encoding gradient $G_y$, the scan is complete and the array 50 is processed to produce an image array 51 which indicates the brightness of each pixel on the display. In the preferred embodiment, this processing includes performing a first Fourier transformation of the image data in array 50 along the readout dimension, and then performing a second Fourier transformation on the resulting data array along the phase encoding dimension. The value of the elements in the resulting data array indicate the brightness of their corresponding pixels in the image array 51.

Figure 5:
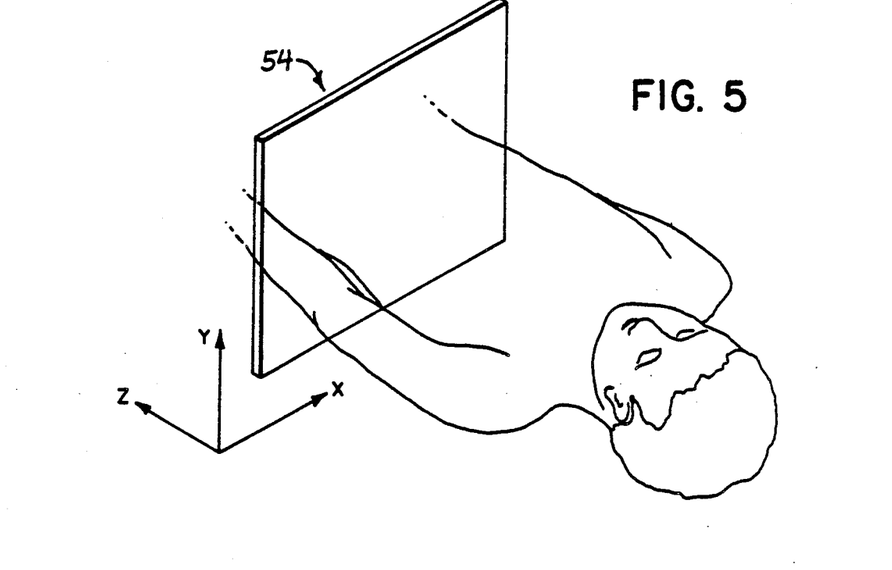
FIG. 5 is a pictorial view of a subject being imaged which shows a slice through the abdomen from which NMR data is acquired.

Just before each row of the image data in array 50 is acquired, a one-dimensional array of motion data 52 is acquired using the motion NMR pulse sequence of FIG. 3. Referring to FIGS. 5 and 6, this motion data is acquired from the slide 54 which is being imaged and it contains a sufficient number of samples (i.e. 128; 256; 512, etc.) to provide the desired position measurement resolution in the vertical, or Y axis direction. In the preferred embodiment, the motion data is acquired from the same vertical and horizontal field of view as the image data and it has the same number of samples. This is not necessary, however, to carry out the present invention.

As each array 52 of motion data is acquired, it is immediately processed to provide a signal indicative of motion. This signal may then be used, for example, to determine the phase encoding gradient value $G_y$ to be used in the next view. In the preferred embodiment, the motion being monitored is that of the anterior abdominal wall, since it quite accurately indicates the motion of other body structures as a function of respiration and because it is relatively easy to identify in the acquired motion NMR data. The abdominal wall contains a layer of fat which produces a peak in the NMR signal and it is adjacent the air outside the patient's body which produces little signal.

While the pulse sequence of FIG. 3 is the preferred means for acquiring the NMR motion signals, many alternatives are possible and may be preferred in some situations. For example, the slice selected by the motion pulse sequence need not be the same as the slice selected by the image pulse sequence, and the slices need not even be oriented along the same axis. Also, while a 90° RF excitation pulse may be employed, smaller flip angles (x) may be used and will interact less with the imaging pulse sequence. While a 180° RF pulse is employed in the motion pulse sequence of FIG. 3, it is also possible to produce a gradient echo signal by the application of a negative lobe on the leading edge of the gradient pulse 143. The advantages of a gradient induced echo over the 180° RF excitation produced echo is a considerable reduction in time necessary to acquire the motion NMR data. Indeed, the total scan time can be reduced even more if the motion data is acquired in the same sequence with the image data. For example, a gradient induced echo signal can be acquired in the same pulse sequence with the image data either in the interval 2 of FIG. 2, just prior to the phase encoding gradient pulse, or in the interval 4 of FIG. 2, just after acquisition of the echo signal $s_1(t)$.

The processing of the motion data in accordance with the present invention is carried out by the computer 114 in response to stored program instructions. These program instructions are illustrated in flow chart form in FIG. 8.

Figure 8:
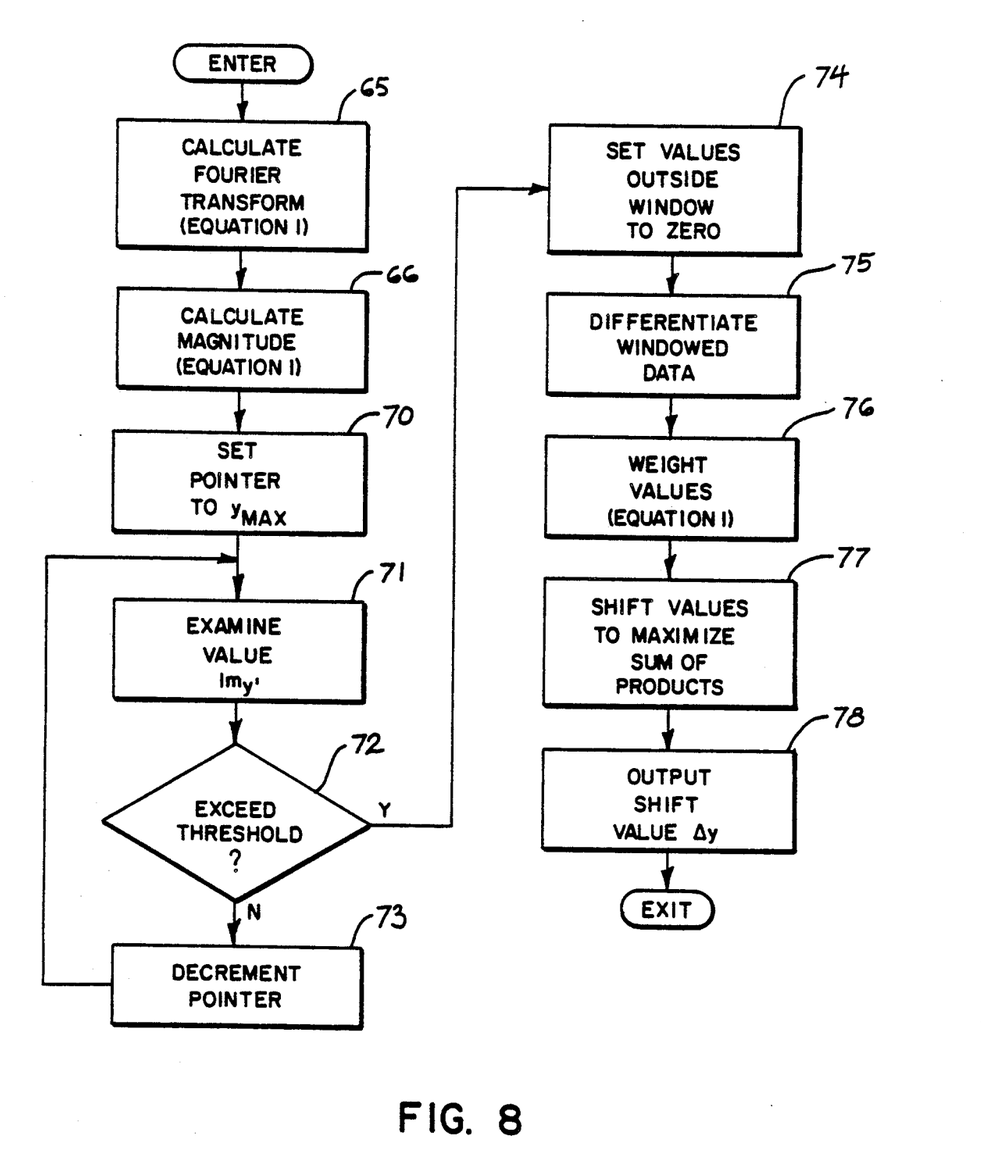
FIG. 8 is a flow chart of a program employed to carry out the present invention.

The first step in processing the motion NMR data is to perform a Fourier transformation of the data in array 52 along its single dimension, the vertical readout dimension as indicated by process block 65.

This transformation may be expressed mathematically as follows for a 256 element array:

$$S_{y'} = \frac{1}{256} \sum_{y=0}^{255} S_y e^{-i2\pi y y'/256} \quad (1)$$

where: $S_y$ is the element of data array 52; and $S_{y'}$ is the corresponding element of transformed data array.

The magnitude of the resulting one-dimensional array of motion data is then calculated at process block 66 to provide an indication of the physical location of the anterior abdominal wall. This calculation can be expressed mathematically as follows for each element of the transformed array:

$$Im_{x'} = \sqrt{(I_{y'})^2 + (Q_{y'})^2} \quad (2)$$

where
$I_{y'}$ is the in-phase value of the transformed array element $S_{y'}$; and
$Q_{y'}$ is the quadrature value of the transformed array element $S_{y'}$.

Figure 7:
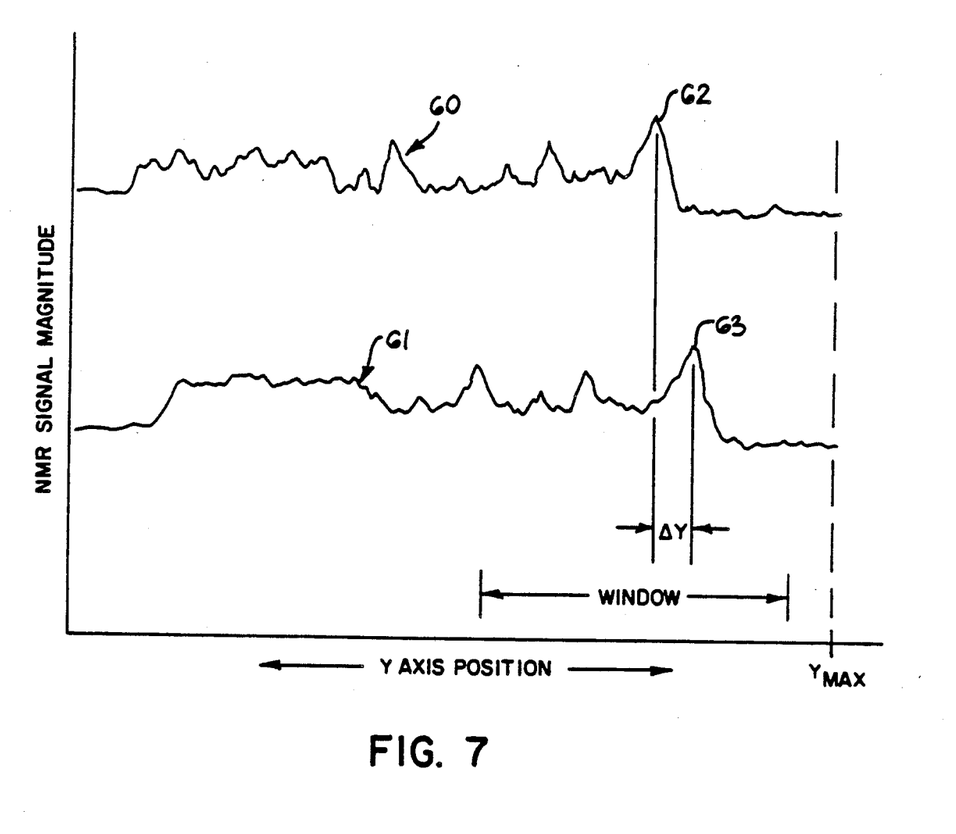
FIG. 7 is a graphic representation of two sets of processed motion data which illustrates the correlation required to produce the desired displacement output value.

An example of such transformed motion data is illustrated in FIG. 7, where the plot 60 is the magnitude of the transformed data for the first motion data pulse sequence, and plot 61 is the magnitude of the transformed data for any subsequent motion data acquired during the same scan. The first plot 60 is used as a reference and the position of each subsequent plot 61 is measured with respect to this reference. For example, the peak in the signal 60 produced by the anterior abdominal wall is indicated at 62, and the same peak in a subsequent set of NMR motion data is indicated at 63. The shift in the position of these peaks ($\Delta Y$) is a direct measurement of the movement of the anterior abdominal wall and this quantity can be scaled to provide a signal which is a direct replacement for the digitized output of a respiration monitor.

Referring again to FIG. 1, the motion NMR data described above is applied to the computer 114 where it is processed to produce the respiration monitor signals $\Delta Y$. These respiration monitor signals can be used internally for artifact suppression purposes, or they can be output at 64 and used externally. For example, the $\Delta Y$ signals which are output at 64 can be used in place of the respirometer transducer, amplifier, and A/D converter shown in FIG. 18 of the above cited U.S. Pat. No. 4,663,591.

Referring again to FIGS. 7 and 8, the measurement of the position shift $\Delta Y$ is performed in two steps: a windowing step and a cross correlation step. The windowing operates to isolate from the motion data in array 52 a small section, or window, which includes the signal peak produced by the anterior abdominal wall. This window is indicated in FIG. 7 and it may be selected by any one of a number of well known techniques. In the preferred embodiment, a pointer is set as indicated at process block 70 in FIG. 8 to read out the last element in the transformed array $Im_{x'}$. This element is related to spin density at the top of the slice 54 and typically is very low because only air is present at this location. A loop is then entered in which successive transformed array elements are examined as indicated at process block 71 until one is found which exceeds a preset threshold as determined at decision block 72. The pointer is decremented at block 73 so that the search begins at the top of the slice 54 and works downward until a signal indicative of the anterior abdominal wall is encountered. When this occurs, all values in the transformed array which are outside the selected window are set to zero as indicated at process block 74. In the preferred embodiment, a window size of 60 elements is used and it is centered on the element which first exceeds the preset threshold.

The next step is to correlate the windowed data from the reference plot 60 with the windowed data from the current plot 61. There are numerous cross correlation techniques known in the art which determine how much one waveform must be shifted to correlate it, or align it, as closely as possible with another waveform. Referring again to FIGS. 7 and 8, in the preferred embodiment both windowed data sets are first differentiated as indicated at process block 75 and then divided by the undifferentiated value plus a constant as indicated at process block 76 to weight the result in favor of the low amplitude, sharply changing signals, which represent the edge of the projection:

$$q_{y'} = \frac{dIm_{y'}}{dy'} (1/Im_{y'} + c) \qquad (3)$$

where:

c is a constant fraction of the peak value of the reference motion data set.

The resulting elements ($q_{y'}$) in the reference waveform window are shifted left or right to determine the position in which the sum of the product of its elements and the corresponding elements in the windowed portion of the current motion data is maximized as indicated by process block 77. In other words, the windowed reference elements are shifted through a series of positions ranging from the left to the right of center, and in each position, the corresponding elements in the two windowed data arrays are multiplied and added together. The resulting computed values define a cross-correlation curve which peaks when the windowed reference data is shifted to the position of best correlation. Each shift position represents an increment of distance along the Y axis and the total number of shifts from center indicates the desired displacement ($\Delta Y$) of the anterior abdominal wall from the reference position. Where higher resolution is desired, an interpolation method may also be used to determine the peak in the correlation curve which usually lies between two discrete shift positions. In any case, the displacement value $\Delta Y$ is output as the indicator of current abdominal wall position, as indicated at process block 78, and it may be employed within the computer 114 to carry out artifact suppression strategies, or it may be output for use as described above.

We claim:

1. A system for providing respiratory phase information during an NMR scan of a subject, which comprises:
    means for producing an NMR motion pulse sequence during the NMR image data scan;
    means for acquiring the NMR motion signals produced by said NMR motion pulse sequence;
    means for processing the motion NMR signals to produce a data set which indicates the position of features in the subject;
    means for locating the position of a specific feature in said data set; and
    means for producing a respiratory signal by correlating the current position of the specific feature with a reference position for that feature.

2. The system as recited in claim 1 in which the means for processing the motion NMR signals includes means for performing a Fourier transformation along a dimension which corresponds to the axis along which the position of features is measured.

3. The system as recited in claim 2 in which the means for producing the NMR motion pulse sequence includes means for producing an RF excitation pulse which produces transverse magnetization in spins contained in the subject, and means for producing a magnetic field gradient along said axis; and the means for acquiring the NMR motion signals includes means for receiving and digitizing the NMR motion signals while said magnetic field gradient is being produced.

4. The system as recited in claim 1 in which the specific feature in the subject is the anterior abdominal wall of a human subject.

5. The system as recited in claim 1 in which the NMR scan is comprised of a series of NMR image pulse sequences and an NMR motion pulse sequence is produced prior to each such NMR image pulse sequence and the data acquired therefrom is used to produce said respiratory signal prior to the production of the following NMR image pulse sequence.

6. The system as recited in claim 1 in which the NMR scan is comprised of a series of NMR image pulse sequences and an NMR motion pulse sequence is produced following each such NMR image pulse sequence and the data acquired therefrom is used to produce said respiratory signal prior to the production of the following NMR image pulse sequence.

* * * * *